United States Patent [19]

Kohli et al.

[11] Patent Number: 4,749,729
[45] Date of Patent: Jun. 7, 1988

[54] EPOXY RESIN COMPOSITIONS CURABLE ABOVE 160 F. AND BELOW 250 F.

[75] Inventors: Dalip K. Kohli, Norwalk; Martin Hauser, Newington, both of Conn.

[73] Assignee: American Cyanamid Company, Stamford, Conn.

[21] Appl. No.: 812,345

[22] Filed: Dec. 23, 1985

Related U.S. Application Data

[63] Continuation-in-part of Ser. No. 622,918, Jun. 21, 1984, abandoned, and a continuation-in-part of Ser. No. 622,919, Jun. 21, 1984, abandoned.

[51] Int. Cl.$^4$ ............................................. C08G 59/40
[52] U.S. Cl. .................................... 523/468; 528/45; 528/94; 528/98; 528/99; 528/117; 528/361; 528/367; 525/504
[58] Field of Search ...................... 523/468; 525/504; 528/45, 94, 117, 98, 99, 361, 367

[56] References Cited

U.S. PATENT DOCUMENTS

| | | | |
|---|---|---|---|
| 4,210,704 | 7/1980 | Chandross et al. | 428/201 X |
| 4,335,228 | 6/1982 | Beitchman et al. | 528/94 X |
| 4,355,058 | 10/1982 | Gras et al. | 528/94 X |
| 4,420,605 | 12/1983 | Kaufman | 528/117 X |

OTHER PUBLICATIONS

Lee et al., *Handbook of Epoxy Resins*, McGraw-Hill, N.Y., 1967 Ed., pp. 20-1 and 20-13; TP1180.E6 L4.

*Primary Examiner*—Earl Nielsen
*Attorney, Agent, or Firm*—Roger S. Benjamin

[57] ABSTRACT

New and improved heat curable compositions are disclosed comprising epoxidic prepolymers and mono- and di-imidazole-carboxamides. The compositions are stable at room temperature, but cure readily at moderate temperatures of substantially less than about 250° F., preferably at about 180° F. to about 200° F. and especially preferably at about 160° F. to about 180° F. The cured neat resins are useful as adhesives and as matrix resins in reinforced composites, with excellent physical properties.

46 Claims, No Drawings

EPOXY RESIN COMPOSITIONS CURABLE ABOVE 160 F. AND BELOW 250 F.

CROSS-REFERENCE TO RELATED APPLICATION

This application is a continuation-in-part of copending applications Ser. Nos. 622,918 and 622,919, both filed on June 21, 1984, now both abandoned.

FIELD OF THE INVENTION

The present invention relates to imidazolecarboxamide curing agents for epoxy resin compositions and to new and improved epoxy resin compositions comprising certain imidazole-carboxamide curing agents, alone, or in further combination with fiber reinforcements. It also relates to new and improved low temperature heat curable epoxy resin compositions having commercially useful shelf lives at room temperatures which are rapidly curable to hard, tack-free states at temperatures substantially below about 200° F., e.g., from 180° F. to below about 250° F. and even from about 160° F. to below about 250° F. and especially from about 160° F. to about 180° F.

BACKGROUND OF THE INVENTION

Epoxy resin compositions are useful to encapsulate electronic components, and as structural adhesives, and the like. Such epoxy resin compositions have found extensive use in the aircraft and aerospace industries, and in other applications where strength, corrosion resistance and light weight are desirable.

Epoxy resin compositions, alone, or in combination with reinforcing fibers, e.g., graphite, carbon, glass, etc., are abundant, and much effort has been expended in improving their properties and characteristics, including the development of many different curing systems.

Amine and polyamine curing agents have received wide acceptance, but the toxicity, low solubility, high exotherm and variable curing rates associated with the most commonly used amines, such as m-phenylenediamine, 4,4'-diaminodiphenyl methane and 4,4'-diaminodiphenyl sulfone, has made further improvement desirable.

One disadvantage in the use of such curing agents is in the need to use elevated temperatures, on the order of 300° to 325° F. to effect curing. Another is their tendency to prematurely activate the compositions, giving them a short pot life at room temperature.

These disadvantages have led to the development of so-called "latent" curing agents, those which are stable at room temperature, but which activate on heating at relatively lower temperatures than the 300° to 325° F. commonly used. As illustrations of latent catalysts can be mentioned, for example, imidazoles in combination with clay fillers, U.S. Pat. No. 4,041,007, in which the clay apparently retards the catalytic activity of the cyclic amine, extending the pot life. In Beitchman et al, U.S. Pat. No. 4,335,228, it is disclosed that useful epoxy curatives comprise the reaction products of an imidazole with a polyisocyanate, such as toluene diisocyanate, which provide epoxy resin compositions which may be cured by heating to temperatures of from about 250° F. to about 400° F. and which exhibit good stability at room temperature. There is no suggestion in said patent that the imidazole-polyisocyanate reaction products may effectively be employed to cure epoxy resin compositions at temperatures substantially below about 250° F. and especially below about 200° F. In Col. 2, line 58, the Beitchman et al patent states that the cure temperature will be from about 250° F. to 400° F. The catalyst of Example 1 was stated to be effective to cure the epoxy resin at temperatures as low as 270° F., but the gloss was improved at higher temperatures of 300° F. This catalyst was also noted to be ineffective at temperatures below 200° F. Moreover, the Beitchman et al patent teaches that imidazole adducts of monoisocyanates are unsuitable for curing epoxy resin compositions.

Also proposed have been esters and salts of imidazoles, U.S. Pat. No. 4,359,370; the sulfonic acid half salt of imidazole, U.S. Pat. No. 4,331,582; the metal imidazolates of U.S. Pat. No. 3,792,016; the salt of imidazole and an alkyl acid phosphate of U.S. Pat. No. 3,642,698; and, of interest, is the use of isocyanate-capped imidazoles to cure polyurethanes, U.S. Pat. No. 4,041,019.

In spite of such developments, there is still unavailable a latent curing agent for epoxies, useful for meeting two special requirements:

(i) it should provide a reasonable degree of cure (>80%) at temperatures substantially below 250° F., and especially below 200° F., preferably at temperatures of above about 180° F. and below about 250° F. and especially preferably at temperatures of above about only 160° F. and below about 250° F. in two hours; and (ii) it should give an adhesive out time (a measure of shelf-life) of at least about 24 hours and preferably at least about 36 hours at 75° F.

Such compositions would meet a long-felt but unsatisfied need in adhesive and coatings end uses, especially if their adhesive bonding strengths are high.

It has now been discovered that certain new and improved imidazole-carboxamide compounds are effective to provide heat-curable epoxy resin compositions having commercially useful shelf lives at room temperatures which may be thermally cured to hard, tack-free states by heating at temperatures substantially below 250° F. The new and improved epoxy resin compositions of the present invention provide neat resin formulations which, after curing, exhibit improved adhesive bond strength.

SUMMARY OF THE INVENTION

It is an object of the present invention to provide new and improved latent epoxy curatives which provide heat-curable compositions having pot or shelf lives of at least about 24 hours at room temperature and which are curable at low temperatures.

In accordance with these and other objects, the present invention provides novel curing agents for epoxy resin compositions comprising certain novel imidazole-carboxamide compounds, namely those represented by the formula:

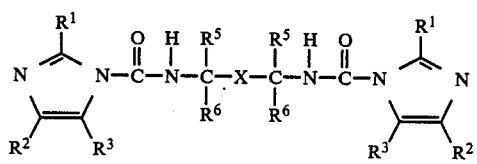

wherein $R^1$, $R^2$, $R^3$, $R^5$ and $R^6$ are each, independently, selected from hydrogen, alkyl or substituted alkyl, and X is a bridging means selected from aliphatic, cycloaliphatic, or aromatic groups. An especially preferred imidazole carboxamide curing agent within the above formula is N,N'-(α,α,α',α'-tetramethylxylylene)bis(1-imidazolecarboxamide). These novel imidazole carboxamide curing agents are generally prepared in accordance with the present invention by reacting the imidazole compound with the corresponding hindered aliphatic diisocyanate at room temperature under anhydrous conditions, refluxing the reaction mixture, and thereafter cooling the reaction mixture to precipitate the imidazole-carboxamide product.

In accordance with another aspect of the present invention, new and improved heat curable epoxy resin compositions having commercially useful shelf lives are provided, said epoxy resin compositions comprising:

(a) an epoxy prepolymer or combination of prepolymers having more than one epoxide group per molecule; and (b) an effective amount to promote cure of said epoxy prepolymer of a latent amine functional curing agent or combination of curing agents selected from imidazole-carboxamide compounds of the formula:

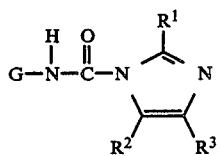

wherein G is selected from

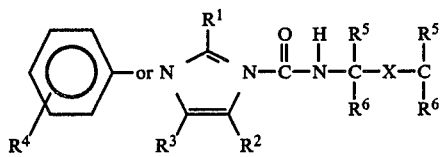

and $R^1$, $R^2$, $R^3$, $R^5$ and $R^6$ are hydrogen, alkyl or substituted alkyl, $R^4$ is hydrogen, hydroxy, halogen, alkyl, substituted alkyl, alkyloxy or substituted alkyloxy, and X is a bridging means selected from aliphatic, cycloaliphatic or aromatic groups.

Generally, and without limitation, the imidazole carboxamide curing agent or agents are employed in an amount of from about 1 to about 25 parts by weight, based upon 100 parts by weight of (a) the epoxidic prepolymer or prepolymer mixture and the curing agent (b). The curable resin compositions of the present invention may generally be prepared by admixing the epoxy prepolymer and the curing agent at from about 32° F. to about 75° F. until thorough mixing is achieved. The neat resin mixture may thereafter be used as an adhesive, coating or potting composition. The neat resin compositions may be thermally cured by heating to temperatures of conventionally employed to cure epoxy resin compositions, e.g., from about 250° to 400° F.

In accordance with another aspect of the present invention, it has been surprisingly discovered that certain of the imidazole-carboxamide curing agents defined above are effective to provide new and improved epoxy resin compositions having commercially useful shelf lives which may be rapidly cured by heating to temperatures substantially below about 250° F., e.g., below about 200° F. In accordance with this aspect, the present invention provides an epoxy resin composition curable at temperatures of more than about 180° F. but less than about 250° F., especially less than about 200° F., and having a useful shelf life at 75° F. of at least about 24 hours, said composition comprising:

(a) an epoxy prepolymer or combination of prepolymers having more than one epoxide group per molecule; and (b) an effective amount to promote cure of said epoxy prepolymer of a latent amine functional curing agent or combination of curing agents selected from imidazole-carboxamide compounds of the formula:

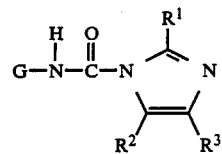

wherein G is selected from

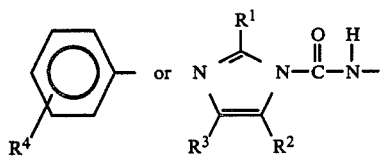

wherein $R^1$, $R^2$ and $R^3$ are hydrogen, alkyl or substituted alkyl, $R^4$ is hydrogen, hydroxy, halogen, alkyl, substituted alkyl, alkyloxy or substituted alkyloxy.

This aspect thus provides a method for low temperature curing of an epoxy resin composition comprising admixing the above-defined imidazole-carboxamide curing agents with an epoxy resin composition and heating the mixture at from about 180° F. to less than about 250° F. until the mixture cures to a hardened, tack-free state.

It has further been unexpectedly discovered that the imidazole-carboxamide curing agents may be employed to provide new and improved epoxy resin compositions which have commercially useful pot or shelf lives at room temperatures, e.g., about 75° F., of at least about 36 hours, and which surprisingly and unexpectedly are curable at temperatures as low as about 160° F. up to about 180° F. in about two hours. Therefore, in accordance with still another aspect of the present invention, there are provided epoxy resin compositions curable at from about 160° F. to about 180° F. and having a useful shelf life at 75° F. of at least about 36 hours, said compositions comprising:

(a) an epoxy prepolymer or combination of prepolymers having more than one epoxide group per molecule; and (b) an effective amount to promote cure of said epoxy prepolymer of a latent amine functional curing agent or combination of curing agents selected from imidazole-carboxamide compounds of the formula:

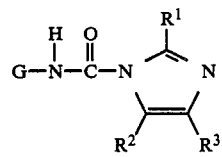

wherein G is selected from

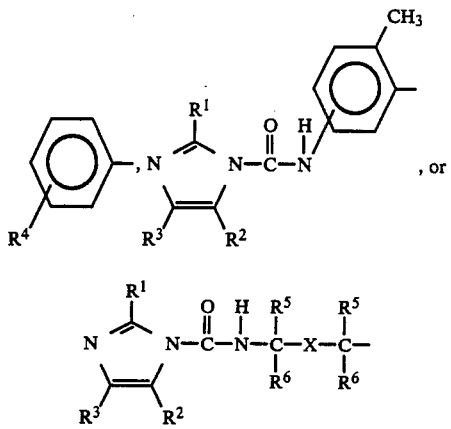

wherein $R^1$, $R^2$, $R^3$, $R^5$ and $R^6$ are hydrogen, alkyl or substituted alkyl, $R^4$ is hydrogen or p-substituted alkyloxy, and X is bridging means selected from aliphatic, cycloaliphatic or aromatic groups.

Thus in accordance with this aspect of the invention there is provided a method for curing an epoxy resin composition at a temperature of from about 160° F. to about 180° F. which comprises admixing the above-identified imidazolecarboxamide curing agents with the epoxy resin composition and heating said mixture at from about 160° F. to about 180° F. until curing of the composition is substantially complete.

The new and improved neat resins of the present invention exhibit improved adhesive bond strength, and they are characterized by superior stability and long shelf-life in the uncured state at ambient temperatures, e.g. 70°–85° F.

Also contemplated are resin-fiber compositions comprising (i) the curable epoxy resin composition as defined above and (ii) a reinforcing amount of a reinforcing fiber, e.g., 20–60 parts by weight of (ii) per 100 parts by weight of (i) and (ii) combined, of glass fibers, graphite fibers, carbon fibers, polyaramid fibers, and the like, in the form of rovings, tows, knitted fabrics, felts, etc. These can be used in well-known ways to form laminates, etc., for structural uses in automobiles, business machines, aircraft, etc.

Other objects and advantages of the present invention will become apparent from the following detailed description of the invention and illustrative working Examples.

DETAILED DESCRIPTION OF THE INVENTION

In general, the resin compositions of the present invention are prepared by mixing the polyepoxide compounds with the imidazole-carboxamides of the above-mentioned formulas in an amount sufficient to provide cure, 1 to 20 parts per hundred resin (phr) by weight.

The epoxy resins suitable for use in the present invention are compounds having more than one epoxide group per molecule available for reaction with the curing agents of the present invention. Such epoxy prepolymers include but are not limited to polyglycidyl ethers of polyvalent phenols, for example pyrocatechol; resorcinol, hydroquinone; 4,4'-dihydroxydiphenyl methane; 4,4'-dihydroxy-3,3'-dimethyldiphenyl methane; 4,4'-dihydroxydiphenyl dimethyl methane; 4,4'-dihydroxydiphenyl methyl methane; 4,4'dihydroxydiphenyl cyclohexane; 4,4'-dihydroxy-3,3'-dimethyldiphenyl propane; 4,4'-dihydroxydiphenyl sulfone; or tris-(4-hydroxyphenyl)methane; polyglycidyl ethers of the chlorination and bromination products of the above-mentioned diphenols; polyglycidyl ethers of novolacs (i.e., reaction products of monohydric or polyhydric phenols with aldehydes, formaldehyde in particular, in the presence of acid catalysts); polyglycidyl ethers of diphenols obtained by esterifying 2 mols of the sodium salt of an aromatic hydrocarboxylic acid with 1 mol. of a dihaloalkane or dihalogen dialkyl ether (U.K. No. 1,017,612); and polyglycidyl ethers of polyphenols obtained by condensing phenols and longchain halogen paraffins containing at least two halogen atoms (U.K. No. 1,024,288).

Other suitable compounds include polyepoxy compounds based on aromatic amines and epichlorohydrin, for example N,N'-diglycidyl-aniline; N,N'-dimethyl-N,N'-diglycidyl-4,4'-diaminodiphenyl methane; N,N,N',N'-tetraglycidyl-4,4'-diaminodiphenyl methane; and N-diglycidyl-4-aminophenyl glycidyl ether. Special mention is made of N,N,N',N'-tetraglycidyl-1,3-propylene-bis(4-aminobenzoate).

Glycidyl esters and/or epoxycyclohexyl esters of aromatic, aliphatic and cycloaliphatic polycarboxylic acids, for example phthalic acid diglycidyl esters and adipic diglycidyl ester and glycidyl esters of reaction products of 1 mol. of an aromatic or cycloaliphatic dicarboxylic acid anhydride and ½ mole of a diol or 1/n mol of a polyol with n hydroxyl groups, or hexahydrophthalic acid diglycidyl esters, optionally substituted by methyl groups, are also suitable.

Glycidyl ethers of polyhydric alcohols, for example of 1,4-butanediol; 1,4-butanediol; glycerol; 1,1,1-trimethylol propane; pentaerythritol and polyethylene glycols may also be used. Triglycidyl isocyanurate; and polyglycidyl thioethers of polyvalent thiols, for example of bis-mercaptomethylbenzene; and diglycidyltrimethylene sulfone, are also suitable.

Preferably the epoxy prepolymer component will be selected from compounds having the idealized formula:

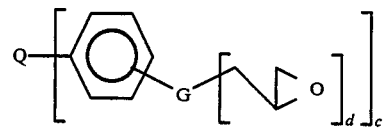

and halogen and alkyl substituted derivatives of such compounds, wherein c is 2, 3 or 4 and equal to the valence of Q; Q is a divalent, trivalent or tetravalent radical; G is

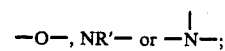

R is hydrogen or alkyl; and d is 1 or 2 depending on the valence of G.

Useful epoxy compounds will include the following:

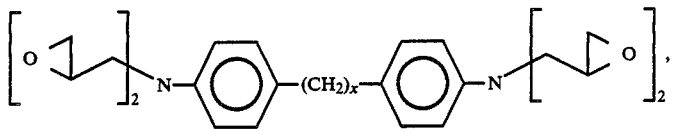

wherein x is an integer from 1 to 4, available commercially (where x=1) as ARALDITE® MY-720 (Ciba-Geigy);

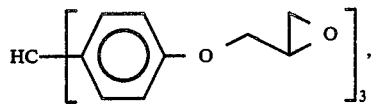

available commercially as XD 7342 (Dow Chemical).

Preferred epoxy compounds are of the formula

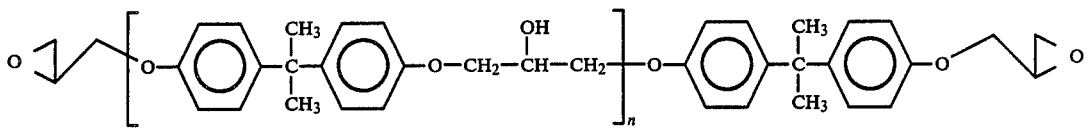

wherein n is a whole number of from about 1 to about 10. Such compounds are available commercially as DER 331 (Dow Chemical), average molecular weight 350–400, or EPON® 828 (Shell).

Also useful are compounds of the formula

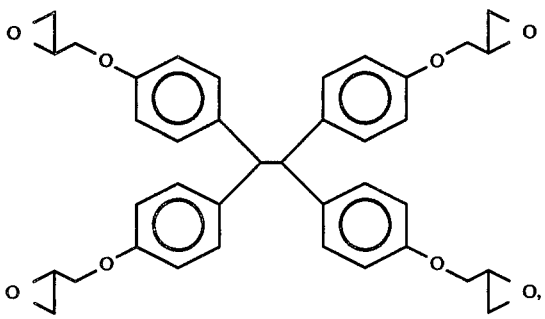

available commercially as EPON® 1031 (Shell); and compounds of the formula

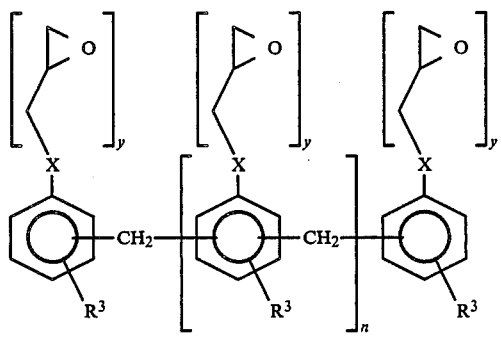

wherein Y is 1 or 2, X is —O— or —NH, $R^3$ is H or $CH_3$ and n is 2 to 8.

Compounds in which X is —O— are available as a mixture under the tradename DEN-438 from Dow Chemical Company.

Useful in addition are triglycidyl ethers of meta- and para-hydroxyaniline, e.g., represented by the formula:

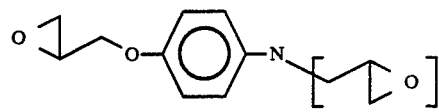

These are available under the tradename ARALDITE® 0500, 0510 from Ciba-Geigy.

In accordance with the present invention, the epoxide prepolymers or mixtures of prepolymers (a) are cured with the imidazole-carboxamide curing agents (b) to provide thermocurable epoxy resin compositions exhibiting improved strength and toughness.

The catalysts used in the invention are prepared by the reaction of imidazole or a derivative thereof with an appropriate isocyanate in a polar aprotic solvent such a tetrahydrofuran, toluene, methylene chloride, or acetonitrile, in accordance with the following equation:

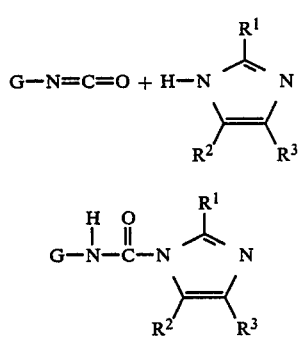

wherein G, $R^1$, $R^2$ and $R^3$ are as above defined. The starting materials are readily available, or can be made by following procedures known in this art. Examples of useful imidazoles are found in the above-mentioned U.S. Pat. No. 4,335,228 and include imidazole, 2-methylimidazole, 2-ethyl-4-methylimidazole, 2-undecylimidazole, 2-heptadecyl imidazole, 2-ethylimidazole, 2,4-dimethylimidazole, and the like. The compounds can also be substituted with various groups inert to epoxy compositions and include for example such substituents as halogen, alkyl, and nitro groups. Among the isocyanates which can be used are monofunctional aromatic isocyanates, such as phenyl isocyanates and alkylphenylisocyanates, alkoxyphenyl isocyanates, nitrophenylisocyanates, etc. Other useful isocyanates are diisocyanates of the formula

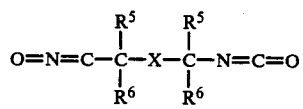

wherein $R^5$, $R^6$ and X are as defined above. These doubly hindered diisocyanates are made according to procedures set forth in U.S. Pat. No. 2,723,265, by phosgenating the corresponding diamines. A preferred family is comprised of the α, α, α′, α′-tetramethylxylylene diisocyanates of U.S. Pat. No. 3,290,350, which can be prepared also by reacting isocyanic acid with an olefin, or in other ways.

The preparation of illustrative imidazole carboxamides will be exemplified in detail hereinafter. Usually, the isocyanate is slowly added to a solution at room temperature of the imidazole in a solvent, such as tetrahydrofuran, acetonitrile, methylene chloride, toluene, or the like. The reagents are preferably in anhydrous form and mixing and reaction are preferably carried out under anhydrous conditions, e.g., under a blanket of nitrogen. The reaction mixture can be stirred until completed, e.g., 2–4 hours, but preferably is heated to reflux for a period of from one-half to two hours, and thereafter cooled to precipitate the imidazole-carboxamide product. The product can be recovered in a conventional manner, e.g., by filtration, to leave the imidazole-carboxamide as a cake. Further purification if desired can be accomplished by recrystallization, or the like.

One preferred family of imidazole-carboxamides is of the formula

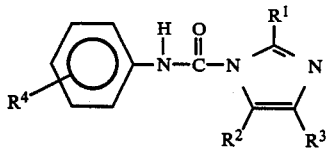

wherein $R^1$, $R^2$ and $R^3$ are hydrogen, alkyl (preferably $C_1$–$C_6$ alkyl) or substituted alkyl, and $R^4$ is hydrogen, hydroxy, halogen, alkyl (preferably $C_1$–$C_6$ alkyl), substituted alkyl, alkyloxy (preferably $C_1$–$C_6$ alkyloxy) or substituted alkyloxy. Especially preferred such compounds are those in which $R^1$, $R^2$ and $R^3$ are hydrogen and $R^4$ is hydrogen, 4—$OCH_3$, or 4—$OC_2H_5$.

A second preferred family of imidazole-carboxamide compounds are those of the formula

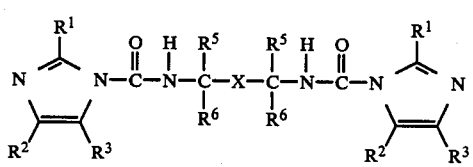

wherein $R^1$, $R^2$, $R^3$, $R^5$ and $R^6$ are hydrogen, alkyl (preferably $C_1$–$C_6$ alkyl), or substituted alkyl, and X is a bridging means selected from aliphatic, cycloaliphatic or aromatic groups (preferably having 2 to 20 carbon atoms). The symbol X is illustrated by groups listed in U.S. Pat. No. 2,723,265. X is not critical per se, but represents a wide variety of forms. Especially preferred are such compounds in which $R^1$, $R^2$ and $R^3$ are hydrogen, $R^5$ and $R^6$ are methyl and X is meta-phenylene,

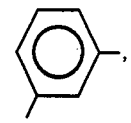

or paraphenylene. See, U.S. Pat. No. 3,290,350.

A third preferred group of imidazole-carboxamide curing agents, are those which have been discovered to provide epoxy resin compositions which are curable at temperatures of about 180° F., and which have useful shelf lives at 75° F. of at least about 24 hours. These latent low temperature imidazole-carboxamide curing agents include imidazole-carboxamides having the formula:

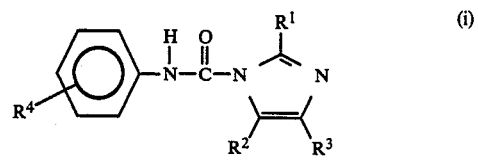

wherein $R^1$, $R^2$, $R^3$ and $R^4$ are as defined above; and

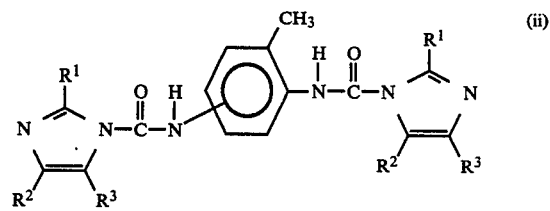

wherein $R^1$, $R^2$ and $R^3$ are the same as defined above. The latter imidazole-carboxamide curing agent (ii) comprises a reaction product of toluene diisocyanate and imidazole or an imidazole derivative. The use of a toluene diisocyanate-imidazole adduct as a curing agent for epoxy resin compositions curable upon heating to elevated temperatures of from about 250° to about 400° F. has been described in the above-mentioned U.S. Pat. No. 4,335,228. Heretofore, however, it was unknown that the use of this curing agent could provide epoxy resin compositions which cure rapidly upon heating at temperatures substantially below 250° F., e.g., 200° F. and, more particularly, at temperatures of above about 180° F., or above as low as about 160° F.

A fourth preferred group of the above-mentioned imidazole-carboxamide curing agents of the present invention are those particular compounds which surprisingly and unexpectedly have been discovered to provide epoxy resin compositions which exhibit useful shelf lives at 75° F. at least about 36 hours and which are rapidly curable at temperatures of above about only 160° F. up to below about 250° F., especially to below about 200° F. or even 180° F. These ultra low temperature latent curing agents include imidazole-carboxamide curing agents of the formulas:

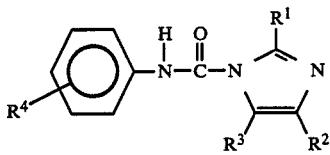

wherein $R^1$, $R^2$ and $R^3$ are each, independently, selected from hydrogen, alkyl or substituted alkyl and $R^4$ is hydrogen or 4-methoxy;

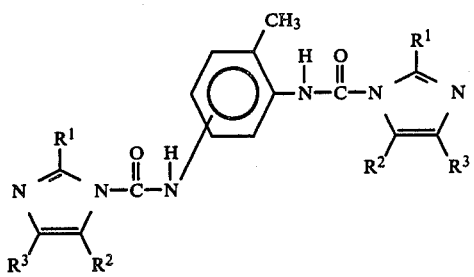

wherein $R^1$, $R^2$ and $R^3$ are as defined above; and

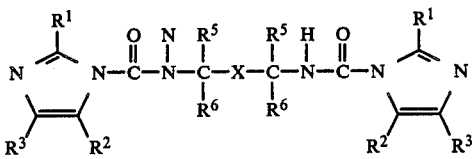

wherein $R^1$, $R^2$, $R^3$, $R^5$ and $R^6$ are as defined above and X is m- or p-phenylene, i.e.,

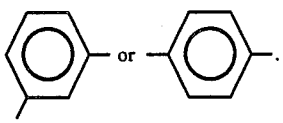

In addition, it is also contemplated to use the imidazole-carboxamides in combination with other curing agents, for example, aromatic polyamine curing agents. For example 1:99 to 99:1 weight/weight combinations of the imidazole-carboxamides with metaphenylenediamine, 4,4'-diamino-diphenylmethane, 3,3'-diaminodiphenyl sulfone, 1,3-propylene bis(p-aminobenzoate), and the like, can be used.

The new and improved epoxy resin compositions of the present invention may be used as neat resins, alone or in admixture with fillers, pigments, dyes, curing catalysts and other conventional additives and processing agents.

The new and improved curing agents of the present invention provide thermally curable neat compositions at low temperatures which exhibit an increase in adhesive bond strength and other important properties.

DESCRIPTION OF THE PREFERRED EMBODIMENTS

In order that those skilled in this art may better understand how the present invention may be practiced, the following examples are provided by way of illustration and not by way of limitation.

The following procedure was used to prepare and cure neat resin compositions: the liquid epoxide prepolymer and the imidazole-carboxamide were mixed at room temperature and the composition was then poured into a shallow pan and cured for 2 hours at the temperature indicated. Properties were determined by the following procedures: The adhesive strength was determined by a tensile shear technique according to ASTM D 1002. The shelf life was determined at 75° F. (room temperature) and taken at the point when the composition had doubled its viscosity ("out time"). The degree of cure was measured by differential scanning calorimetry (DSC).

EXAMPLES 1-3

(a) Imidazole-Carboxamide of Phenylisocyanate

Phenylisocyanate was slowly added to a solution in acetonitrile of imidazole at 75° F. After 1 hour, the product was recovered by filtration. It had a melting point of 115°–117° C.

(b) Epoxy resin Compositions of Imidazole-Carboxamide of Phenylisocyanate

Three compositions containing differing quantities of the adduct were formulated and cured at 160° F., following the general procedure set forth above. The formulations used and the results obtained are set forth in Table 1:

TABLE 1

| Curable Epoxy Resin Compositions | | | |
|---|---|---|---|
| Example | 1 | 2 | 3 |
| Composition (parts by weight) | | | |
| Bisphenol A diglycidyl ether[a] | 93.5 | 89.8 | 86.5 |
| Reaction product of imidazole and phenylisocyanate | 6.5 | 10.2 | 13.5 |
| Properties | | | |
| Degree of Cure by DSC, % | 85 | 88 | 93 |
| Out Time at 75° F., hours | 36 | 36 | 24 |

[a]Dow Chemical Co. DER 331

The compositions have adequate cure rates at 160° F. and good shelf life.

EXAMPLES 4-6

(a) Imidazole-Carboxamide of p-Methoxyphenylisocyanate p-Methoxyphenylisocyanate was slowly added to a solution of imidazole according to the procedure of Example 1. It had a melting point of 131°–132° C.

(b) Epoxy resin Compositions of Imidazole-carboxamide of p-Methoxyphenylisocyanate Three compositions containing differing quantities of the adduct were formulated and cured by the general procedure set forth above at 160° F. The formulations used and the results obtained are set forth in Table 2.

TABLE 2

| Curable Epoxy Resin Compositions | | | |
|---|---|---|---|
| Example | 4 | 5 | 6 |
| Composition (parts by weight) | | | |
| Bisphenol-A diglycidyl ether[a] | 92.4 | 88.4 | 84.7 |
| Reaction Product of imidazole and p-methoxyphenylisocyanate | 7.6 | 11.6 | 15.3 |
| Properties | | | |
| Degree of cure by DSC, % | 78 | 82 | 87 |
| Out Time at 75° F., hours | 72 | 48 | 48 |

[a]Dow Chemical Co. DER 331.

The curative of this example has high activity and very good shelf life.

EXAMPLES 7-8

(a) Bis-imidazole-carboxamide of α,α,α',α'-tetramethylxylylenediisocyanate (TMXDI)

TMXDI was added slowly to a solution of imidazole according to the procedure of Example 1. The product had a melting point of 132°-133° C.

(b) Epoxy resin Compositions of bis-Imidazole Carboxamide of TMXDI

Two compositions containing differing quantities of the adduct were formulated and cured at 160° F. by the general procedure set forth above and the results are set forth in Table 3.

TABLE 3

| Curable Epoxy Resin Compositions | | |
| --- | --- | --- |
| Example | 7 | 8 |
| Composition (Parts by weight) | | |
| Bisphenol-A diglycidyl ether[a] | 92.6 | 89.3 |
| Reaction product of imidazole and α, α, α', α'-tetramethyl-xylylenediisocyanate | 7.4 | 10.7 |
| Properties | | |
| Degree of cure by DSC, % | 58 | 69 |
| Out Time at 75° F., hours | 200 | 200 |

[a]Dow Chemical Co., DER 331.

These compositions were especially outstanding in shelf-lives.

To demonstrate the unique suitability of compounds according to the present invention, a closely related compound was prepared. This had the formula

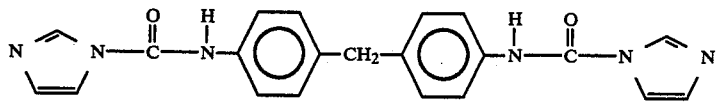

and was the reaction product of imidazole and p,p¹-diphenylmethane diisocyanate, m.p. 181°-182° C. This was ineffective to cure bisphenol-A diglycidyl ether at 160° F. in 2 hours.

When the imidazole-carboxamide of Examples 1-3 is used in an epoxy adhesive formulation, at about 11 parts by weight per 10 parts of epoxy, and bonded in a ½" lap between aluminum plates (0.064 in. 2024-T3 ALCLAD) and tested at −67° F., 70° F., 140° F. and 100° F., shear strengths ranged between 2050 psi and 4180 psi, the highest strengths being obtained at room temperature.

The following N-(p-substituted phenyl)-1-imidazolecarboxamides were prepared:

| Example No. | Curing Agent |
| --- | --- |
| 9 | N—phenyl-1-imidazolecarboxamide |
| 10 | N—(p-methoxyphenyl)-1-imidazolecarboxamide |
| 11 | N—(p-chlorophenyl)-1-imidazolecarboxamide |
| 12 | N—(p-ethoxyphenyl)-1-imidazolecarboxamide |
| 13 | N—(p-propoxyphenyl)-1-imidazolecarboxamide |
| 14 | N—(p-isopropoxyphenyl)-1-imidazolecarboxamide |
| 15 | N—(p-butoxyphenyl)-1-imidazolecarboxamide; and |
| 16 | N—(p-hydroxyphenyl)-1-imidazolecarboxamide. |

The N-phenyl-, N-p-methoxyphenyl-, N-p-chlorophenyl- and N-p-ethoxyphenyl-substituted imidazolecarboxamides, Examples 9-12, were prepared by reaction of imidazole with the corresponding monoarylisocyanates, which are commercially available, in accordance with the method of Examples 1-3.

The corresponding isocyanates for the N-p-propoxy-, N-p-isopropoxy- and N-p-butoxy-substituted phenyl-1-imidazolecarboxamides, Examples 13-15, were not on hand, and the corresponding isocyanate starting materials were prepared by the method summarized by the following reaction sequence:

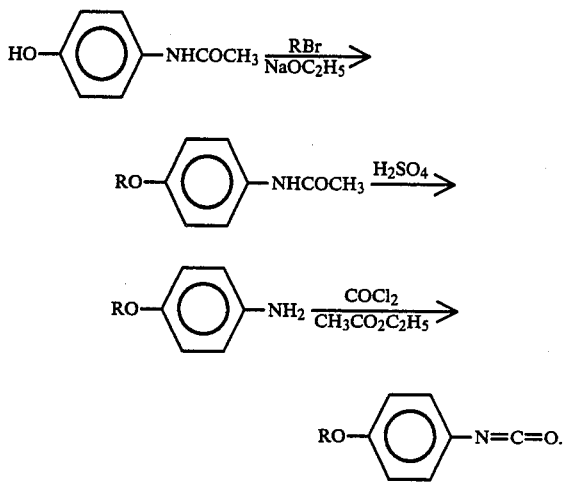

More particularly, these N-(p-alkoxyphenyl)-1-imidazolecarboxamides were generally prepared as follows:

(i) Synthesis of p-Alkoxyacetanilides p-Hydroxyacetanilide (1.0 moles) and the appropriate alkyl bromide (1.2 moles) were added to a solution of sodium (1.2 g-atoms) in absolute alcohol (700 ml). The resulting solution was heated at reflux for 5 hours and the alcohol was then stripped in vacuo. The residual solid was washed thoroughly with water, dried, and used directly in the following procedure.

(a) p-Alkoxyanilines

General Method

The crude anilide and 25% sulfuric acid (950 ml) were heated at reflux for 2 hours. The solution was chilled and the precipitated amine sulfate was filtered, dried, and then dissolved in hot water (600 ml). The aqueous solution was made strongly alkaline with 20% sodium hydroxide and the oil which separated was dissolved in ether. The ethereal solution was dried over magnesium sulfate and the ether was distilled. Fractional distillation of the residue in vacuo gave the product anilines as colorless liquids. Overall yields for the two-step process were 40-50%.

p-Propoxyaniline: bp 87°-8°/2 mm
p-Isopropoxyaniline: bp 71.5°-72°/2 mm
p-Butoxyaniline: bp 96°-9°/9 mm (b) p-Alkoxyphenylisocyanates General Method A solution of p-alkoxyaniline (25 g) in ethyl acetate (200 ml) was phosgenated at such a rate that the temperature did not exceed 35°. Additional phosgene was bubbled into the mixture throughout the addition. After addition was complete, the flow of phosgene was discontinued and the solution was heated at reflux for 0.5 hr. The ethyl acetate was distilled in vacuo and the residue was fractionated to give 60–70% of the product isocyanates as colorless liquids.

p-Propoxyphenylisocyanate: bp 78°–9°/2 mm
p-Iospropoxyphenylisocyanate: bp 58°–9°/2 mm
p-Butoxyphenylisocyanate: bp 78°–80°/2 mm (c) N-(p-Substituted phenyl)-1-imidazole-carboxamides General Method A solution of aryl isocyanate (0.1 mole) in anhydrous THF (30 ml) was slowly added to a solution of imidazole (0.1 mole) in anhydrous THF (30 ml) stirred under nitrogen. After addition was complete, the solution was heated at reflux for 0.5 hr. and then chilled. The resulting precipitate was filtered, dried, and recrystallized from THF or THF:hexane under anhydrous conditions. Yields of purified product were 75–85%. The hygroscopic carboxamides should be stored in a desiccator to prevent reversion to the starting materials.

The N-(p-substituted phenyl)-1-imidazolecarboxamides represented by the formula:

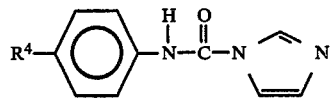

prepared in accordance with the methods outlined above and in Examples 1–3, were analyzed as follows:

| Example Number | $R^4$ | mp °C. | Chemical Analysis Calculated/found | | |
|---|---|---|---|---|---|
| | | | C | H | N |
| 9 | H | 115°–117° C. | nd* | nd | nd |
| 10 | $OCH_3$ | 133–5° C. | 60.83 | 5.07 | 19.35 |
| | | | 61.09 | 5.20 | 19.05 |
| 11 | Cl | 146–7.5° C. | 54.18 | 3.61 | 18.96 |
| | | | 54.07 | 3.65 | 18.39 |
| 12 | $OC_2H_5$ | 158–9° C. | 62.34 | 5.63 | 18.18 |
| | | | 62.51 | 5.87 | 17.66 |
| 13 | $OC_3H_7$ | 126–8° C. | 63.67 | 6.12 | 17.14 |
| | | | 64.19 | 6.20 | 16.98 |
| 14 | $OC_3H_7$—i | 102.5–4° C. | 63.67 | 6.12 | 17.14 |
| | | | 64.15 | 6.19 | 16.87 |
| 15 | $OC_4H_9$ | 93–5 | 64.86 | 6.56 | 16.21 |
| | | | 65.22 | 6.52 | 16.40 |

*nd - not determined.

The p-hydroxyphenylisocyanate starting material for the N-(p-hydroxyphenyl)-1-imidazolecarboxamide, Example 16, was prepared in accordance with the following reaction sequence:

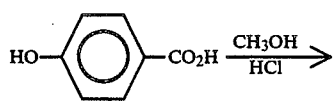

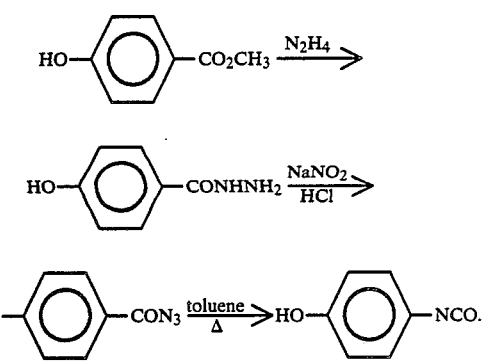

More particularly, the N-(p-hydroxyphenyl)-1-imidazolecarboxamide was prepared as follows:

Synthesis of N-(p-hydroxyphenyl)-1-imidazole-carboxamide (i) Synthesis of Methyl-p-hydroxybenzoate p-Hydroxybenzoic acid (50 g, 0.36 mole), absolute methanol (200 ml), and concentrated sulfuric acid (6 ml) were heated at reflux for 3 hrs. The solution was cooled and poured into water (1000 ml). The precipitate was filtered and dried; mp 122°–5°. Yield: 45 g (82%).

(ii) p-Hydroxybenzhydrazide

A mixture of the crude methyl ester (45 g, 0.30 mole) and hydrazine hydrate (23 g, 0.46 mole) was heated at reflux for 2 hours. The solution was chilled and the precipitate was filtered and dried; mp 266° dec. Yield: 42 g (93%).

(iii) p-Hydroxybenzazide

A solution of the crude hydrazide (15.2 g, 0.1 mole) in 5% hydrochloric acid (300 ml) was chilled to 2° and treated, over 1 hour, with a solution of sodium nitrite (7.6 g, 0.11 mole) in water (40 ml). The temperature was held below 5° during the addition. The resulting solution was kept at 5° for 0.5 hr. and was then extracted with four 50 ml portions of ether. The ethereal solution was dried over calcium sulfate and the ether was distilled. The residual solid was dissolved in alcohol and precipitated with water; mp 126°–7° dec.

Yield: 10.5 g (62%).

(iv) p-Hydroxyphenylisocyanate and the imidazol adduct

A solution of the azide (4.9 g, 0.03 mole) in dry toluene (100 ml) was heated at reflux for 2 hours under nitrogen. The solution was cooled to 25° and treated with a solution of imidazole (2.04 g, 0.03 mole) in dry THF (15 ml). After 0.5 hr. the precipitate was filtered and dried; mp 210° dec. Yield: 5.6 g (92%). A suitable recrystallization solvent could not be found.

Anal. Calcd. for $C_{10}H_9N_3O_2$: C, 59.11; H, 4.43; N, 20.69. Found: C 59.30; H, 4.57, N, 20.22.

Each of the N-(p-substituted phenyl)-1-imidazole-carboxamides of Examples 9–16 were evaluated as epoxy curatives by mixing an amount of the imidazole-carboxamide compound sufficient to provide 2.5 parts by weight per 100 parts by weight of the epoxy resin of free imidazole in an epoxy resin comprising the diglycidyl ether of bisphenol-A(DER 331, Dow Chemical Company) and by heating the mixture for 90 minutes at 180° F.

In accordance with the evaluation procedures, the degree of cure of the epoxy resin-curing agent composition was measured on an arbitrary scale of 0–5 as follows:

| Cure No. | Degree of Cure |
| --- | --- |
| 0 | no increase in viscosity |
| 1 | slight increase in viscosity |
| 2 | greater viscosity increase |
| 3 | tacky gum |
| 4 | some hardness, flexible, slight tack |
| 5 | hard, tack-free | state after heating at 180° F. for 90 minutes. In addition, the sample compositions were evaluated for useful shelf life by mixing the epoxy resin and curing agent specified, and thereafter permitting the mixture to stand under ambient conditions until a small amount of sample would no longer flow off the end of a spatula. Time to gelation was noted in days. The results obtained for the compositions are set forth in TABLE 4 as follows:

TABLE 4

N—(p-substituted phenyl)-1-Imidazolecarboxamide Curing Agents for Epoxy Resin Compositions Curable at 180° F.

| Example | 9 | 10 | 11 | 12 | 13 | 14 | 15 | 16 |
| --- | --- | --- | --- | --- | --- | --- | --- | --- |
| Degree of Cure | 5 | 5 | 5 | 5 | 5 | 5 | 5 | 5 |
| Shelf Life, Days | 2 | 6–7 | ≦1 | 11–13 | 4–5 | 2–3 | 2 | 5 |

Each of N-(p-substituted phenyl)-1-imidazole-carboxamide curing agents of Examples 9–16 were found to effectively cure an epoxy resin composition to a hard, tack-free state at temperatures of about 180° F. in less than two hours. With the exception of the N-(p-chlorophenyl)-1-imidazolecarboxamide which exhibited a variable shelf-life, all of the low temperature curing agents of Examples 9–16 exhibited commercially useful shelf lives at room temperatures of about 75° F. of greater than 24 hours.

EXAMPLE 17

(a) Preparation of 1,1'-(4-methyl-1,3-phenylene)-bis(1-imidazolecarboxamide)

A solution of 2,4-toluene diisocyanate (0.025 mole) in anhydrous tetrahydrofuran (25 ml) was added over 0.5 hr. to a solution of imidazole (0.05 mole) in anhydrous THF (75 ml) stirred under nitrogen. The resulting solution was kept 0.5 hr. at 25° and was then heated at reflux for 1 hour. The precipitate obtained on chilling was recrystallized from anhydrous THF to give a white, crystalline solid; mp 148°–52° (30% yield).

Anal. Calcd. for $C_{15}H_{14}N_6O_2$: C, 58.07; H, 4.52; N, 27.10. Found: C, 58.83; H, 4.76; N, 26.65.

(b) Epoxy Resin Composition of Imidazole-carboxamide of 2,4-toluene diisocyanate An epoxy resin composition comprising the diglycidyl ether of bisphenol-A(DER 331, Dow Chemical Company) and an amount of the N,N'-(4-methyl-1,3-phenylene) bis(1-imidazolecarboxamide) sufficient to provide 2.5 parts by weight of free imidazole per 100 parts by weight of epoxy resin. The composition was cured at 180° F. for 90 minutes and tested in accordance with the methods of Examples 9–16. The composition was effectively cured at 180° F. to yield a degree of cure of 5 on the arbitrary scale and exhibited a commercially useful shelf-life of from 3–4 days at room temperatures of about 75° F.

Each of the above-mentioned patents, applications and publications are specifically incorporated herein by reference. Although the present invention has been described with reference to certain preferred embodiments, modifications or changes may be made therein by those skilled in this art. For example, instead of the diglycidyl ether of 4,4'-dihydroxy-3,3'-dimethylphenyl propane, N,N,N',N'-tetra(glycidyl-4,4'-diaminodiphenyl)methane can be used as the epoxy prepolymer component. Instead of curing at 160° F. and 180° F., curing can be effected at 200° F., 220° F., 230° F. and 240° F. All such obvious modifications are within the scope and spirit of the present invention as defined by the appended claims.

What is claimed is:

1. In a method for curing an epoxy resin composition comprising an epoxy prepolymer or combination of prepolymers having more than one epoxide group per molecule, said method comprising:

(a) intimately admixing in the epoxy resin composition an effective amount to promote cure of a latent amine-functional curing agent or combination of curing agents selected from imidazole-carboxamide compounds of the formula:

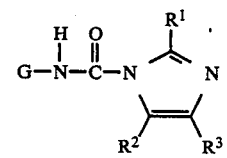

wherein G is selected from

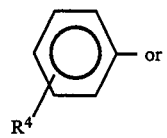

or

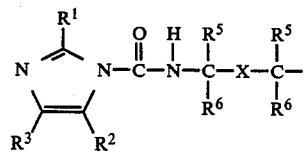

where $R^1$, $R^2$, $R^3$, $R^5$ and $R^6$ are hydrogen, alkyl or substituted alkyl, $R^4$ is hydrogen, alkyl, substituted alkyl, alkyloxy or substituted alkyloxy, and X is a bridging means selected from aliphatic, cycloaliphatic or aromatic groups or

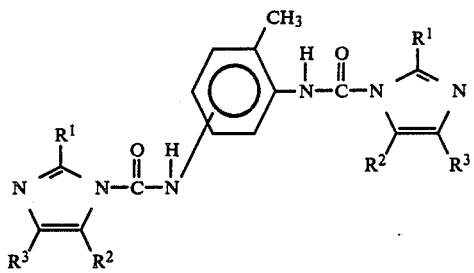

wherein $R^1$, $R^2$ and $R^3$ are hydrogen, alkyl or substituted alkyl, or a mixture of said compounds; and (b) heating the mixture of step (a) until curing of said mixture is substantially complete, the improvement which comprises heating at a temperature in the range of from about 160° F. to less than about 250° F.

2. A method as defined in claim 1 wherein heating is carried out at a temperature in the range of from about 160° F. to about 200° F.

3. A method as defined in claim 1 wherein the epoxy prepolymer or combination of prepolymers comprises from 75 to 99 parts by weight and the curing agent or combination of curing agents comprises from 1 to 25 parts by weight per 100 parts by weight of prepolymer and curing agent.

4. A method as defined in claim 1 wherein the epoxy prepolymer is selected from (i) aromatic compounds of the formula:

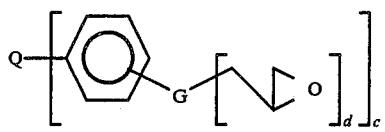

and halogen and alkyl substituted derivatives of such compounds, wherein c is 2, 3 or 4 and equal to the valence of Q, Q is a divalent, trivalent or tetravalent radical; G is

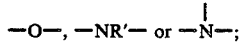

R' is hydrogen or alkyl; and d is 1 or 2 and equal to the valence of G; (ii) cycloaliphatic polyepoxide compounds, or a mixture of (i) and (ii).

5. A method as defined in claim 4 wherein the epoxy prepolymer comprises a compound of the formula:

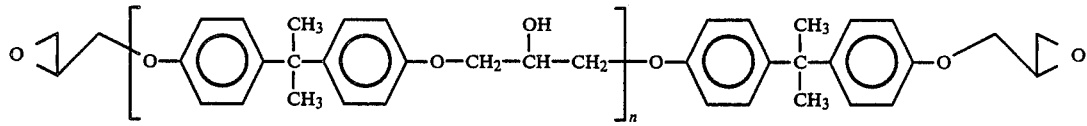

wherein n is O or a whole number of from about 1 to about 10.

6. A method as defined in claim 5 wherein, in the epoxy prepolymer, the average molecular weight is 350 to 400.

7. A method as defined in claim 1 wherein said curing agent is of the formula

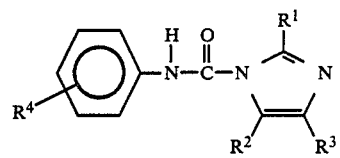

wherein $R^1$, $R^2$ and $R^3$ are hydrogen, alkyl or substituted alkyl, and $R^4$ is hydrogen, alkyl, substituted alkyl, alkyloxy or substituted alkyloxy.

8. A method as defined in claim 7 wherein $R^1$, $R^2$ and $R^3$ are hydrogen and $R^4$ is hydrogen or 4-OCH$_3$.

9. A method as defined in claim 8 wherein $R^1$, $R^2$, $R^3$ and $R^4$ are hydrogen.

10. A method as defined in claim 9 wherein $R^1$, $R^2$ and $R^3$ are hydrogen and $R^4$ is 4-OCH$_3$.

11. A method as defined in claim 1 wherein said curing agent is of the formula:

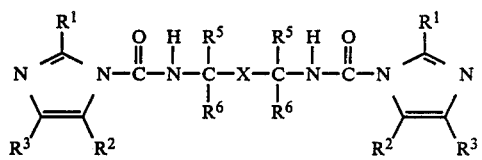

wherein $R^1$, $R^2$, $R^3$, $R^5$ and $R^6$ are hydrogen, alkyl or substituted alkyl, and X is a bridging means selected from aliphatic, cycloaliphatic or aromatic groups.

12. A method as defined in claim 11 wherein $R^1$, $R^2$ and $R^3$ are hydrogen, $R^5$ and $R^6$ are methyl, and X is m-phenylene or p-phenylene.

13. In a method for curing an epoxy resin composition comprising an epoxy prepolymer or combination of prepolymers having more than one epoxide group per molecule, and method comprising:

(a) intimately admixing in the epoxy resin composition an effective amount to promote cure of a latent amine functional curing agent or combination of curing agents selected from an imidazole-caboxamide compound of the formula:

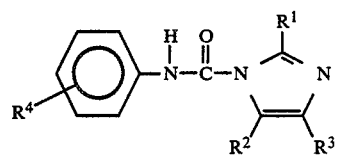

wherein $R^1$, $R^2$ and $R^3$ are, independently, hydrogen, alkyl or substituted alkyl and $R^4$ is hydrogen, hydroxy, halogen, alkyl, substituted alkyl, alkyloxy or substituted alkyloxy or of the formula:

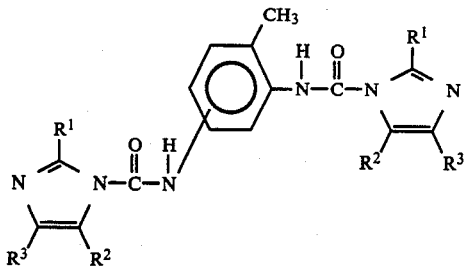

wherein $R^1$, $R^2$ and $R^3$ are hydrogen, alkyl or substituted alkyl, or a mixture of said compounds; and
(b) heating the mixture of step (a) until curing of said mixture is substantially complete, the improvement which comprises heating at a temperature in the range of from about 180° F. to less than about 250° F.

14. A method as defined in claim 13 wherein heating is carried out at a temperature in the range of from about 180° F. to about 200° F.

15. A method as defined in claim 13 wherein the epoxy prepolymer or combination of prepolymers comprises from 75 to 99 parts by weight and the curing agent or combination of curing agents comprises from 1 to 25 parts by weight per 100 parts by weight of prepolymer and curing agent.

16. A method as defined in claim 13 wherein the epoxy prepolymer is selected from (i) aromatic compounds of the formula:

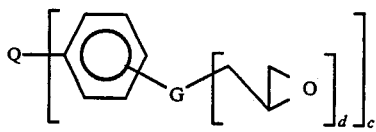

and halogen and alkyl substituted derivatives of such compounds, wherein c is 2, 3 or 4 and equal to the valence of Q, Q is a divalent, trivalent of tetravalent radical; G is

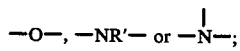

R' is hydrogen or alkyl; and d is 1 or 2 and equal to the valence of G; (ii) cycloaliphatic polyepoxide compounds, or a mixture of (i) and (ii).

17. A method as defined in claim 15 wherein the epoxy prepolymer comprises a compound of the formula:

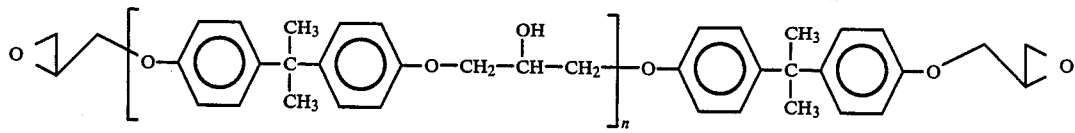

wherein n is O or a whole number of from about 1 to about 10.

18. A method as defined in claim 17 wherein, in the epoxy prepolymer, the average molecular weight is 350 to 400.

19. A method as defined in claim 13 wherein in said curing agent $R^1$, $R^2$ and $R^3$ are hydrogen and $R^4$ is hydrogen.

20. A method as defined in claim 13 wherein in said curing agent $R^1$, $R^2$ and $R^3$ are hydrogen and $R^4$ is 4-hydroxy.

21. A method as defined in claim 13 wherein in said curing agent $R^1$, $R^2$ and $R^3$ are hydrogen and $R^4$ is 4-chloro.

22. A method as defined in claim 13 wherein in said curing agent $R^1$, $R^2$ and $R^3$ are hydrogen and $R^4$ is 4-methoxy.

23. A method as defined in claim 13 wherein in said curing agent $R^1$, $R^2$ and $R^3$ are hydrogen and $R^4$ is 4-ethoxy.

24. A method as defined in claim 13 wherein in said curing agent $R^1$, $R^2$ and $R^3$ are hydrogen and $R^4$ is 4-propoxy.

25. A method as defined in claim 13 wherein in said curing agent $R^1$, $R^2$ and $R^3$ are hydrogen and $R^4$ is 4-isopropoxy.

26. A method as defined in claim 13 wherein in said curing agent $R^1$, $R^2$ and $R^3$ are hydrogen and $R^4$ is 4-butoxy.

27. In a method for curing an epoxy resin composition comprising an epoxy prepolymer or combination of prepolymers having more than one epoxide group per molecule, said method comprising:
(a) intimately admixing in the epoxy resin composition an effective amount to promote cure of a latent amine-functional curing agent or combination of curing agents selected from imidazole-carboxamide compounds of the formula:

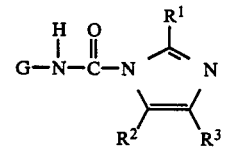

wherein G is selected from

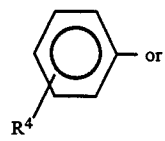

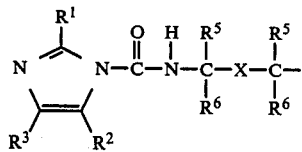

where $R^1$, $R^2$, $R^3$, $R^5$ and $R^6$ are hydrogen, alkyl or substituted alkyl, $R^4$ is hydrogen, alkyl, substituted alkyl, alkyloxy or substituted alkyloxy, and X is a bridging means selected from aliphatic, cycloaliphatic or aromatic groups or

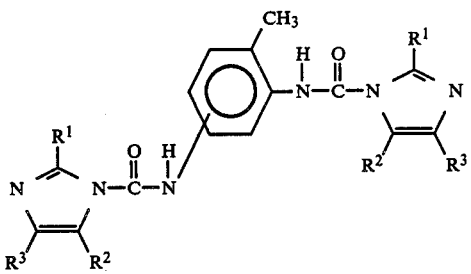

wherein $R^1$, $R^2$ and $R^3$ are hydrogen, alkyl or substituted alkyl, or a mixture of said compounds; and
(b) heating the mixture of step (a) until curing of said mixture is substantially complete, the improvement which comprises heating at a temperature in the range of from about 160° F. to about 180° F.

28. A method as defined in claim 27 wherein the epoxy polymer or combination of prepolymers comprises from 75 to 99 parts by weight and the curing agent or combination of curing agents comprises from 1 to 25 parts by weight per 100 parts by weight of preopolymer and curing agent.

29. A method as defined in claim 27 wherein the epoxy prepolymer is selected from (i) aromatic compounds of the formula:

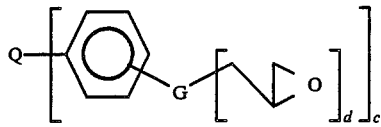

and halogen and alkyl substituted derivatives of such compounds, wherein c is 2, 3 or 4 and equal to the valence of Q, Q is a divalent, trivalent or tetravalent radical; G is

R' is hydrogen or alkyl; and d is 1 or 2 and equal to the valence of G; (ii) cycloaliphatic polyepoxide compounds, or a mixture of (i) and (ii).

30. A method as defined in claim 29 wherein the epoxy prepolymer (a) comprises a compound of the formula:

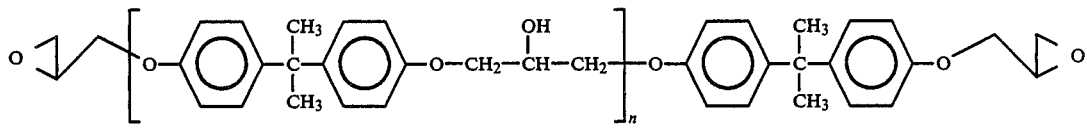

wherein n is 0 or a whole number of from about 1 to about 10.

31. A method as defined in claim 30 wherein, in the epoxy prepolymer, the average molecular weight is 350 to 400.

32. A method as defined in claim 27 wherein said curing agent (b) is of the formula

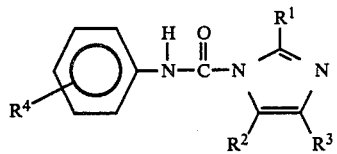

wherein $R^1$, $R^2$ and $R^3$ are hydrogen, alkyl or substituted alkyl, and $R^4$ is hydrogen, alkyl, substituted alkyl, alkyloxy or substituted alkyloxy.

33. A method as defined in claim 32 wherein $R^1$, $R^2$ and $R^3$ are hydrogen and $R^4$ is hydrogen or 4-OCH$_3$.

34. A method as defined in claim 33 wherein $R^1$, $R^2$, and $R^3$ and $R^4$ are hydrogen.

35. A method as defined in claim 33 wherein $R^1$, $R^2$ and $R^3$ are hydrogen and $R^4$ is 4-OCH$_3$.

36. A method as defined in claim 27 wherein said curing agent is of the formula:

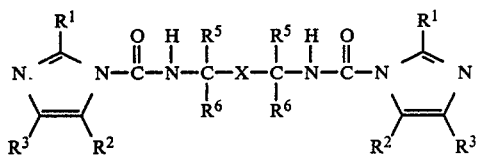

wherein $R^1$, $R^2$, $R^3$, $R^5$ and $R^6$ are hydrogen, alkyl or substituted alkyl, and X is a bridging means selected from aliphatic, cycloaliphatic or aromatic groups.

37. A method as defined in claim 36 wherein $R^1$, $R^2$ and $R^3$ are hydrogen, $R^5$ and $R^6$ are methyl, and X is m-phenylene or p-phenylene.

38. An epoxy resin composition comprising:
(a) an epoxy prepolymer or combination of prepolymers having more than one epoxide group per molecule; and
(b) an effective amount to promote cure of said epxoy prepolymer of a latent amine functional curing agent or combination of curing agents selected from imidazole-carboxamide compounds of the formula:

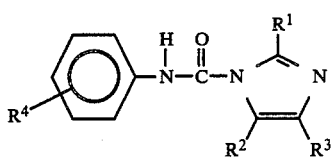

wherein $R^1$, $R^2$, and $R^3$ are hydrogen, alkyl or substituted alkyl, and $R^4$ is hydrogen, alkyl, substituted alkyl, alkyloxy or substituted alkyloxy.

39. A composition as defined in claim 38 wherin $R^1$, $R^2$ and $R^3$ are hydrogen and $R^4$ is hydrogen or 4-OCH$_3$.

40. A composition as defined in claim 39 wherein $R^1$, $R^2$, $R^3$ and $R^4$ are hydrogen.

41. A composition as defined in claim 39 wherein $R^1$, $R^2$ and $R^3$ are hydrogen and $R^4$ is 4-OCH$_3$.

42. A curable resin-fiber matrix composition comprising (i) an epoxy resin composition as defined in claim 38 and (ii) an effective, reinforcing amount of a reinforcing fiber.

43. A curable resin-fiber matrix as defined in claim 42, wherein said reinforcing fiber comprises graphite or carbon.

44. A curable resin-fiber matrix composition comprising:

(i) an epoxy resin composition comprising:

(a) an epoxy prepolymer or combination of prepolymers having more than one epoxide group per molecule; and (b) an effective amount to promote cure of said epoxy prepolymer of a latent amine functional curing agent or combination of curing agents selected from imidazole-carboxamide compounds of the formula:

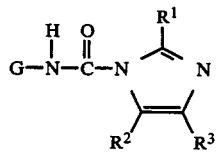

wherein G is selected from

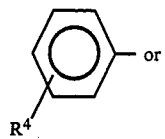

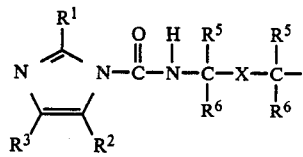

wherein $R^1$, $R^2$, $R^3$, $R^5$ and $R^6$ are hydrogen, alkyl or substituted alkyl, $R^4$ is hydrogen, alkyl, substituted alkyl, alkyloxy or substituted alkyloxy, and x is a bridging means selected from aliphatic, cycloaliphatic or aromatic groups, or a mixture of said compounds; and (ii) an effective, reinforcing amount of a reinforcing fiber.

45. A curable resin-fiber matrix as defined in claim 44, wherein said reinforcing fiber comprises graphite or carbon.

46. A curable resin-fiber matrix composition as defined in claim 44 wherein the latent amine functional curing agent is one or more imidazole-carboxamides of the formula:

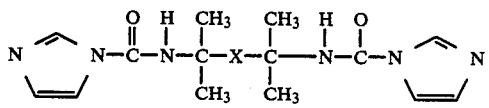

wherein X is m-phenylene or p-phenylene.

* * * * *